(12) United States Patent
Döring

(10) Patent No.: US 9,315,845 B2
(45) Date of Patent: Apr. 19, 2016

(54) PROCESS FOR THE CONTINUOUS ENZYMATIC HYDROLYSIS OF PROTEINS

(71) Applicant: DMK Deutsches Milchkontor GmbH, Zeven (DE)

(72) Inventor: Sven-Rainer Döring, Zeven (DE)

(73) Assignee: DMK Deutsches Milchkontor GmbH, Zeven (DE)

( * ) Notice: Subject to any disclaimer, the term of this patent is extended or adjusted under 35 U.S.C. 154(b) by 0 days.

(21) Appl. No.: 14/564,592

(22) Filed: Dec. 9, 2014

(65) Prior Publication Data

US 2015/0159189 A1  Jun. 11, 2015

(30) Foreign Application Priority Data

Dec. 10, 2013 (EP) ..................................... 13196559

(51) Int. Cl.
  *C12P 21/06* (2006.01)
  *A23J 3/34* (2006.01)
  *C12M 1/26* (2006.01)
  *C12M 1/40* (2006.01)

(52) U.S. Cl.
  CPC ................. *C12P 21/06* (2013.01); *A23J 3/341* (2013.01); *A23J 3/343* (2013.01); *A23J 3/346* (2013.01); *C12M 21/18* (2013.01); *C12M 33/14* (2013.01); *A23V 2300/28* (2013.01)

(58) Field of Classification Search
  None
  See application file for complete search history.

(56) References Cited

U.S. PATENT DOCUMENTS

| | | | | |
|---|---|---|---|---|
| 4,427,658 A | * | 1/1984 | Maubois | A23J 3/343 426/41 |
| 5,691,165 A | * | 11/1997 | Nielsen | A23J 3/343 426/41 |
| 2013/0233788 A1 | * | 9/2013 | Vizvardi | B01D 7/0009 210/490 |
| 2015/0240267 A1 | * | 8/2015 | Anthony | C12P 7/16 435/160 |

FOREIGN PATENT DOCUMENTS

| | | |
|---|---|---|
| EP | 2 168 665 a1 | 3/2010 |
| EP | 2 286 900 A1 | 2/2011 |
| EP | 2 615 067 A2 | 7/2013 |
| JP | H11-128693 A | 5/1999 |

OTHER PUBLICATIONS

Noble J. GE ZeeWeed MBR Technology for Pharmaceutical Wastewater Treatment. Membrane Technology Sep. 2006, pp. 7-9.*

* cited by examiner

*Primary Examiner* — Ralph Gitomer
(74) *Attorney, Agent, or Firm* — Dilworth & Barrese, LLP

(57) ABSTRACT

A continuous process and device for the enzymatic hydrolysis of proteins is disclosed.

14 Claims, 1 Drawing Sheet

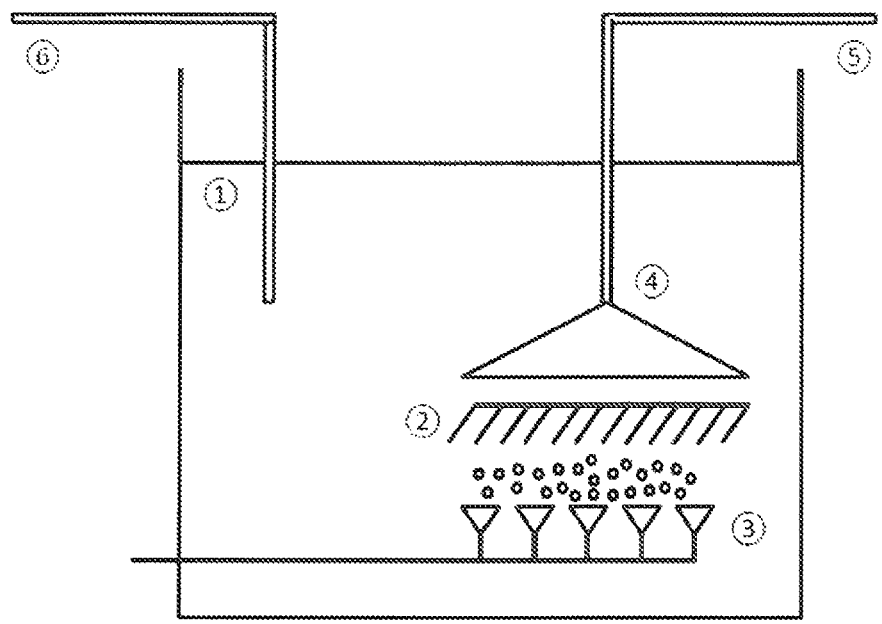

PROCESS FOR THE CONTINUOUS ENZYMATIC HYDROLYSIS OF PROTEINS

This application claims priority to EPO 13 196 559.2 filed Dec. 10, 2013.

FIELD OF THE INVENTION

The invention is in the area of foodstuffs and relates to a new reactor and a new process for continuous enzymatic hydrolysis of proteins.

PRIOR ART

Protein hydrolysates are mixtures of amino acids, dipeptides and oligopeptides with low molecular weight up to about 1,000, which are produced on an industrial scale by treating proteins with alkalis or preferably proteases. Depending on the raw material, the hydrolysates are cosmetic raw materials or foodstuffs; the latter are obtained on the basis of whey or milk. They are important intermediates, for example for the production of milk powder.

In the foodstuffs area, protein hydrolysates are usually produced by adding proteases, for example pepsin, to protein concentrates, for example concentrates with a high content of whey proteins, and conducting hydrolysis at about 30 to 35° C. There is a change of pH during hydrolysis, therefore regulators are added to the system.

For example, a method is known from EP 0588841 B1 (Danmark Protein), in which whey protein concentrates first undergo thermal treatment, are treated with proteases and the hydrolysate is submitted to ultrafiltration on a membrane with a sharpness of separation of 10,000. The protein hydrolysates migrate into the permeate, whereas the enzymes remain in the retentate.

A device and a method are known from EP 0566877 B1 (Nestlé), in which hydrolysis is carried out in two steps, namely for a short period in a vat and for a longer time in a stream tube.

EP 0671126 B1 (Morinaga Milk) relates to the production of whey protein hydrolysates using an enzyme cocktail, wherein lactose is removed by ultrafiltration before hydrolysis, and the inactivated enzymes are removed from the products after hydrolysis, also using ultrafiltration.

The problem in the production of protein hydrolysates according to the prior art is that the progress of hydrolysis, i.e. the degree of hydrolysis, is difficult to monitor and therefore the reaction times are often too long. If the batch is as it were left to itself, it may be that it is not until the product is discharged from the reactor that it is found that a bad batch has been produced. It is obvious that it would be desirable to monitor the hydrolysis process better and thus be able to set the reaction times precisely.

An alternative is to lead the charge at a pressure from 3 to 10 bar over an ultrafiltration membrane that has a size of separation from about 500 to 1,000 Da. As enzymes have a molecular weight of approx. 25,000 Da and proteins have a molecular weight from about 18,000 to 36,000 Da, the permeate obtained in this way still only contains hydrolysis product, whereas the retentate can be recycled. However, even this method is not completely satisfactory, because during circulation by pumping, the enzymes are exposed to such high transfer velocities that the mechanical loading leads to inactivation.

The aim of the invention was therefore to provide an improved method for enzymatic hydrolysis of proteins, which in particular can be operated continuously and which reliably avoids the disadvantages of the prior art described at the beginning, especially inactivation of the enzymes through mechanical damage. Another aim of the invention was to develop a corresponding device in which the method can be carried out.

DESCRIPTION OF THE INVENTION

The invention firstly relates to a device for carrying out a hydrolysis reaction, comprising the following components:
(a) a reaction vessel for receiving the educts to be hydrolysed and the enzymes (1),
(b) a seaweed membrane (2),
(c) an aerating device (3),
(d) a device for withdrawing liquids (4),
(e) a product discharge line (5), and
(f) an educt feed line (6),
wherein
(i) the seaweed membrane (2) is arranged in the bottom third of the reaction vessel (1),
(ii) the aerating device (3) is located beneath and the device for withdrawing liquids (4) is located above the seaweed membrane (2), and
(iii) the product discharge line (5) is connected to the device for withdrawing liquids (4).

The product discharge line is preferably in direct communication with the permeate space of the membrane. The device may moreover have a separate feed line, via which for example a buffer solution for adjusting the pH is fed in. Furthermore, the device may have suitable automatic control technology.

A second aspect of the invention relates to a continuous process for production of protein hydrolysates, in which proteins are submitted in aqueous solution to enzymatic hydrolysis, characterized in that
(i) the reaction vessel is aerated from the bottom, thereby producing convection,
(ii) the reaction mixture, moving as a result of convection, is led through a seaweed UF membrane present in the reaction vessel,
(iii) the resultant permeate containing the hydrolysis products is withdrawn immediately after passing through the membrane and is discharged from the reactor, whereas the retentate, containing unreacted proteins and enzymes, remains in the reaction vessel and
(iv) the amount of permeate withdrawn is compensated by continuous feed of fresh starting product.

It was found, surprisingly, that seaweed membranes are particularly suitable for separating the valuable products quantitatively from a mixture of unreacted proteins and hydrolysis products thereof and the enzymes used as catalysts. Instead of high flow rates, which would lead to inactivation of the enzymes as a result of mechanical damage, slow convection is sufficient, which circulates the reaction mixture and has the effect that mixture flows continuously through the membrane present in the reaction vessel. Moreover, after it leaves the membrane, the permeate containing the protein hydrolysates is withdrawn continuously, whereas unreacted starting material and the enzymes remain in the retentate and may react further. Owing to the slow convection, the enzymes remain active and the amount of permeate withdrawn is replaced by feeding in an equal amount of fresh solution of the starting products. This reliably avoids development of cavitation effects and hence damage to the ingredients. Impairment that can be attributed to the shearing force of the impellers of pumps that are otherwise usually employed is avoided.

With the device according to the invention and the process according to the invention, protein hydrolysates are produced continuously, without constantly supplying fresh enzyme or having to service the equipment. The continuous operating mode also makes it possible, by regular sampling, to establish the degree of hydrolysis in the withdrawn product at any time.

BRIEF DESCRIPTION OF THE DRAWING

The present invention will be described in greater detail with reference to the accompanying drawing which illustrates a continuous hydrolysis reactor according to the invention for carrying out the process, also according to the invention.

DESCRIPTION OF THE PREFERRED EMBODIMENTS

Raw Materials

Basically all common protein sources are suitable for production of the protein hydrolysates obtainable by the process. Therefore both vegetable and animal raw materials may come into consideration, for example wheat proteins, pea proteins, almond proteins or silk proteins; however, whey or milk proteins are especially preferable, as these are permitted for foodstuff purposes. The proteins may be obtained from the raw materials by processing and extraction techniques familiar to a person skilled in the art. Preferably aqueous concentrates are used, which have a protein content of at least 50 wt %, preferably about 60 to about 90 wt %. Whey or milk protein concentrates with a protein content of at least 60 wt % and preferably about 75 to about 85 wt % are especially preferred.

Enzymes

The hydrolysis process is usually carried out using proteases. These enzymes, which catalyse the cleavage of the peptide bond, include for example acrosin, aminopeptidase B, bromelain, calpain I, carboxypeptidase A, cathepsin A, cathepsin B, cathepsin D, cathepsin E, cathepsin K, chymotrypsin, collagenase, dipeptidyl peptidase 4, Dispase, elastase, factor IIa, factor Xa, ficin, gpr-endopeptidase, kallikrein, MBTPS1, papain, plasmin, Prepilin type IV peptidase, prolyl-oligopeptidase, proteinase K, proteasome, renin, secretases (alpha-, beta- and gamma-secretase), thermolysin, thrombin, and urokinase. However, the use of pepsin and/or trypsin is much preferred. Hydrolysis is preferably carried out at a temperature in the region of the optimum activity of the enzymes, which is as a rule at about 10 to about 45° C., preferably about 25 to about 40° C. and especially about 30 to about 35° C.

Ultrafiltration

Ultrafiltration means filtration through membranes with a pore size<0.1 µm. It is a purely physical, i.e. mechanical membrane separation technique, which operates by the principle of mechanical size exclusion: all particles in the fluids that are larger than the membrane pores are retained by the membrane. The essential feature, in the sense of the invention, is that so-called seaweed membranes are used, which until now have only found application in the area of wastewater treatment. These are membranes that have the form of long threads and are arranged in bundles, so that they move like seaweed in the gentle current of the reaction system and owing to their enormous surface area have an exceptionally high efficiency. Corresponding products are commercially available from General Electric. Preferably, membranes are used that have a size of separation from about 500 to about 10,000 Da and preferably from about 1,000 to about 5,000 Da.

Process Variables

As explained above, the principle of the process according to the invention is that instead of working with high transfer rates, which cause the enzymes to be disrupted and inactivated, slow convection is set up in the reaction vessel, in such a way that the direction of flow of the reaction mixture means it must pass through a seaweed membrane. In the current, the fibres of the membrane move slowly to and fro, which on the one hand leads, as a result of the large surface area, to a high separation efficiency, but on the other hand is accompanied by low mechanical loading, so that inactivation of the enzymes is reliably avoided. The convection is created by aeration of the reaction mixture from the bottom, which at the same time has a self-cleaning effect and prevents fouling. For this, air or an inert gas is injected through one, several but preferably a large number of nozzles, the pressure as a rule being at about 1.1 to about 1.5 bar and preferably at about 1.2 bar. Moreover, it has proved advantageous to arrange the aeration nozzles directly beneath the membrane and select spacing not greater than 30 cm, preferably about 10 to about 25 cm. The optimum distance depends on the size of the reaction vessel and can be set by a person skilled in the art without applying an inventive step. In these circumstances, the reaction mixture is namely driven directly onto the membrane, which improves the efficiency of the process considerably.

Instead of the aerating device, it is also possible to use an impeller or a pump with open operation, so as to achieve gentle streams or convection over the membrane.

The reaction mixture, which, driven by the convection, goes into the region of the seaweed membrane, is separated into a permeate and a retentate. The protein hydrolysates, which have a low molecular weight, pass through the ultrafiltration membrane and are drawn to the suction device, which produces a constant suction of about 0.5 to about 0.9 bar and preferably about 0.8 bar, and are ejected, whereas unreacted proteins and enzymes remain in the retentate—thus simply do not pass through the ultrafiltration membrane—and remain in the reaction space, to continue the reaction there.

In this way, a stream that consists almost entirely of protein hydrolysates of the desired molecular weight is constantly withdrawn from the reaction vessel. In order to configure a continuous process, therefore fresh starting product is fed in. The particular advantage of this mode of operation is that the essential steps—aeration of the reactor to bring about convection, ultrafiltration by means of a seaweed membrane and withdrawal of the permeate—all take place in the liquid phase, thus within the reaction vessel. An important aspect of the invention is that the process according to the invention causes a reversal of the pressure conditions: the permeate side is under negative pressure, so that the permeate is drawn into the permeate space of the membrane. On the other hand the retentate side is at normal pressure, so that the permeate cannot be forced through.

The device according to the invention for carrying out the process, also according to the invention, is explained in more detail in FIG. 1. The symbols used there are also used in the following patent claims.

The invention claimed is:

1. A continuous process for production of protein hydrolysates, in which proteins are submitted to enzymatic hydrolysis in aqueous solution, comprising the following steps:
   (i) aerating a reaction vessel containing a reaction mixture of proteins and enzymes from the bottom, thereby producing convection, (ii) leading the reaction mixture, moving as a result of convection, through a seaweed ultrafiltration membrane present in the reaction vessel to obtain a permeate and a retentate, (iii) withdrawing the resultant permeate containing the hydrolysis products immediately after passing through the membrane and is discharged from the reactor, whereas the retentate, containing unreacted proteins and enzymes, remains in the reaction vessel, and (iv) compensating the amount of permeate withdrawn by continuous feed of fresh starting proteins.

2. The process of claim 1, wherein said proteins selected from the group consisting of whey proteins, lactoproteins, wheat proteins, pea proteins, almond proteins and silk proteins.

3. The process of claim 1, wherein said proteins are aqueous protein concentrates having a protein content of at least 50 wt. %.

4. The process of claim 1, wherein said protein is a whey or milk protein concentrate having a protein content of at least 60 wt. %.

5. The process of claim 1, wherein said enzymes are proteases.

6. The process of claim 5, wherein the protease is pepsin and/or trypsin.

7. The process of claim 1, wherein the hydrolysis process is carried out at a temperature in the region of the optimum activity of the enzymes.

8. The process of claim 7, wherein the hydrolysis process is carried out at about 30 to 35° C.

9. The process of claim 1, wherein said seaweed ultrafiltration membrane has a size of separation from 500 to 10,000 Dalton.

10. The process of claim 9, wherein said seaweed ultrafiltration membrane has a size of separation from 1,000 to 5,000 Dalton.

11. The process of claim 1, wherein the aerating of the reaction vessel takes place with air or an inert gas, which is injected by nozzles.

12. The process of claim 1, wherein the aerating takes place with a pressure from 1.1 to 1.5 bar.

13. The process of claim 1, wherein the aerating is located directly beneath the seaweed membrane and the spacing is not more than 30 cm.

14. The process of claim 1, wherein the permeate is withdrawn with a pressure from 0.5 to 0.9 bar.

* * * * *